United States Patent
Cardon et al.

(10) Patent No.: US 11,525,628 B2
(45) Date of Patent: Dec. 13, 2022

(54) PROCESS FOR PRODUCING BIOMETHANE FROM A BIOGAS STREAM, COMPRISING SOLIDIFICATION OF THE IMPURITIES

(71) Applicant: L'Air Liquide, Societe Anonyme pour l'Etude et l'Exploitation des Procedes Georges Claude, Paris (FR)

(72) Inventors: Guillaume Cardon, Poissy (FR); Antonio Trueba, Charenton le Pont (FR); Solene Valentin, Meudon (FR)

(73) Assignee: L'Air Liquide, Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 598 days.

(21) Appl. No.: 16/582,207

(22) Filed: Sep. 25, 2019

(65) Prior Publication Data

US 2020/0096254 A1 Mar. 26, 2020

(30) Foreign Application Priority Data

Sep. 25, 2018 (FR) ...................................... 1858702

(51) Int. Cl.
*C07C 7/10* (2006.01)
*C07C 7/12* (2006.01)
(Continued)

(52) U.S. Cl.
CPC ............ *F25J 3/0219* (2013.01); *B01D 53/02* (2013.01); *B01D 53/1475* (2013.01); *B01D 53/229* (2013.01); *B01D 53/261* (2013.01); *B01D 53/265* (2013.01); *C07C 7/005* (2013.01); *C07C 7/10* (2013.01); *C07C 7/12* (2013.01); *C07C 7/144* (2013.01); *C10L 3/103* (2013.01); *C10L 3/104* (2013.01); *C10L 3/105* (2013.01);
(Continued)

(58) Field of Classification Search
None
See application file for complete search history.

(56) References Cited

U.S. PATENT DOCUMENTS

| | | | |
|---|---|---|---|
| 2012/0064565 A1* | 3/2012 | Liu ........................... | G01F 3/30 435/287.1 |
| 2018/0066199 A1* | 3/2018 | Krylowicz ............... | C10J 3/721 |
| 2018/0112142 A1* | 4/2018 | Foody ..................... | C10L 3/105 |

FOREIGN PATENT DOCUMENTS

| | | |
|---|---|---|
| DE | 10 2013 008535 | 11/2014 |
| EP | 1 308 502 | 5/2003 |

(Continued)

OTHER PUBLICATIONS

Berg, Benjamin, "Efficient liquid biomethane production with cryogenic upgrading," Gas for Energy, Jan. 2017, pp. 26-29.
(Continued)

*Primary Examiner* — Tam M Nguyen
(74) *Attorney, Agent, or Firm* — Yan Jiang

(57) ABSTRACT

Process for producing biomethane from a biogas stream including methane, carbon dioxide and at least one impurity chosen from ammonia, volatile organic compounds, water, sulfur-based impurities ($H_2S$) and siloxanes. A biogas stream is dried, the at least one impurity is at least partially removed by solidification and removal of the impurity. The methane and the carbon dioxide contained in the biogas obtained from the second step are separated so as to produce a biomethane stream and a $CO_2$ stream.

14 Claims, 3 Drawing Sheets

(51) Int. Cl.
*F25J 3/02* (2006.01)
*B01D 53/02* (2006.01)
*B01D 53/14* (2006.01)
*B01D 53/22* (2006.01)
*B01D 53/26* (2006.01)
*C07C 7/00* (2006.01)
*C07C 7/144* (2006.01)
*C10L 3/10* (2006.01)

(52) U.S. Cl.
CPC .............. C10L 3/106 (2013.01); F25J 3/0233 (2013.01); F25J 3/0266 (2013.01); *B01D 2252/204* (2013.01); *C10L 2200/0259* (2013.01); *C10L 2200/0263* (2013.01); *C10L 2200/0286* (2013.01); *C10L 2200/0469* (2013.01); *C10L 2290/08* (2013.01); *C10L 2290/30* (2013.01); *C10L 2290/46* (2013.01); *C10L 2290/542* (2013.01); *C10L 2290/544* (2013.01); *C10L 2290/548* (2013.01); *F25J 2205/20* (2013.01); *F25J 2205/30* (2013.01); *F25J 2205/40* (2013.01); *F25J 2210/66* (2013.01); *F25J 2220/66* (2013.01); *F25J 2220/68* (2013.01); *F25J 2230/30* (2013.01); *F25J 2260/20* (2013.01)

(56) References Cited

FOREIGN PATENT DOCUMENTS

FR 2 960 445 12/2011
FR 3 050 655 11/2017

OTHER PUBLICATIONS

French Search Report and Written Opinion for FR 1858702, dated Jul. 2, 2019.

\* cited by examiner

PROCESS FOR PRODUCING BIOMETHANE FROM A BIOGAS STREAM, COMPRISING SOLIDIFICATION OF THE IMPURITIES

CROSS-REFERENCE TO RELATED APPLICATIONS

This application claims the benefit of priority under 35 U.S.C. § 119 (a) and (b) to French patent application No. FR 1858702, filed Sep. 25, 2018, the entire contents of which are incorporated herein by reference.

BACKGROUND

Field of the Invention

The present invention relates to a process for producing biomethane from a biogas stream comprising methane, carbon dioxide and at least one impurity chosen from ammonia, volatile organic compounds, water, sulfur-based impurities ($H_2S$) and siloxanes.

The invention relates in particular to the purification of biogas, for the purpose of producing biomethane in accordance with the specifications for injection into a natural gas network.

Related Art

Biogas is the gas produced during the degradation of organic matter in the absence of oxygen (anaerobic fermentation), also referred to as methanization. This may be natural degradation—it is thus observed in marshland or in household waste landfills—but the production of biogas may also result from the methanization of waste in a dedicated reactor referred to as a methanizer or digester.

By virtue of its main constituents—methane and carbon dioxide—biogas is a powerful greenhouse gas; at the same time, it also constitutes a source of renewable energy that is appreciable in the context of the increasing scarcity of fossil fuels.

Biogas predominantly contains methane ($CH_4$) and carbon dioxide ($CO_2$) in proportions that may vary according to the way in which it is obtained, but also contains, in smaller proportions, water, nitrogen, hydrogen sulfide, oxygen and other organic compounds, in trace amount.

Depending on the organic matter that has been degraded and on the techniques used, the proportions of the components differ, although on average biogas includes, on a dry gas basis, from 30 to 75% methane, from 15 to 60% $CO_2$, from 0 to 15% nitrogen, from 0 to 5% oxygen and trace compounds.

Biogas is put to profitable use in various ways. It may, after light treatment, be put to profitable use near the production site in order to supply heat, electricity or a mixture of both (cogeneration); the high carbon dioxide content reduces its calorific value, increases the costs of compression and transport and limits the economic benefit of this way putting it to profitable use nearby.

Purifying biogas to a greater degree allows it to be put to broader use; in particular, extensive purification of biogas yields a biogas that has been purified to the specifications of natural gas and which can be substituted for the latter; biogas thus purified is known as "biomethane". Biomethane thus supplements the natural gas resources with a renewable proportion produced within the territories; it can be put to exactly the same uses as natural gas of fossil origin. It can be fed into a natural gas network, a vehicle filling station; it can also be liquefied to be stored in the form of liquefied natural gas (LNG), etc.

The ways in which biomethane is put to profitable use are determined according to the local context: local energy requirements, possibilities for putting it to profitable use as a biomethane fuel, and whether there is a natural gas transport or distribution network nearby, in particular. By creating synergy between the various parties operating in a given territory (farmers, manufacturers, civic authorities), the production of biomethane assists the territories in acquiring greater energy autonomy.

There are a number of steps that need to be completed between collecting the biogas and obtaining biomethane, the end-product that can be compressed or liquefied.

In particular, there are several steps needed prior to the treatment which is aimed at separating out the carbon dioxide in order to produce a stream of purified methane.

SUMMARY OF THE INVENTION

The present invention proposes to provide an improved process for producing biomethane.

DETAILED DESCRIPTION OF THE INVENTION

One solution of the present invention is a process for producing biomethane from a biogas stream comprising methane, carbon dioxide and at least one impurity chosen from ammonia, volatile organic compounds, water, sulfur-based impurities ($H_2S$) and siloxanes, comprising: a first step of drying the biogas stream; a second step of at least partial removal of said impurity contained in the dried biogas stream by solidification and removal of the impurity; and a third step of separating the methane and the carbon dioxide contained in the biogas obtained from the second step so as to produce a biomethane stream and a $CO_2$ stream.

Figure 1:
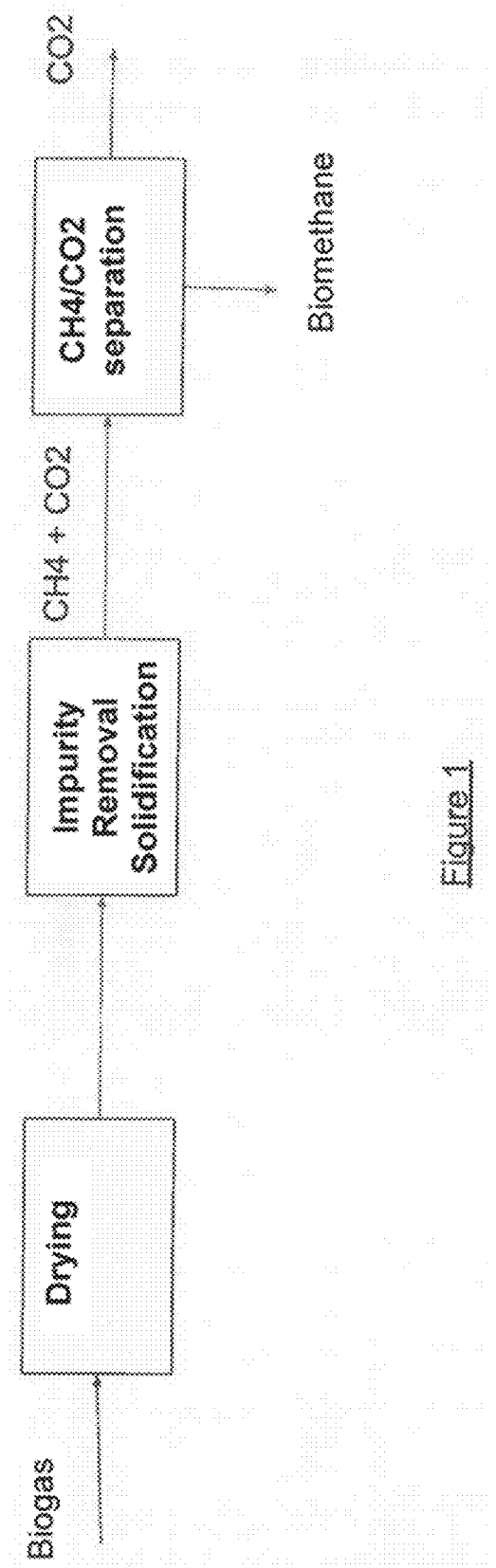
FIG. 1 is a flow chart of an aspect of the invention.

These three steps are illustrated by FIG. 1.

Figure 2:
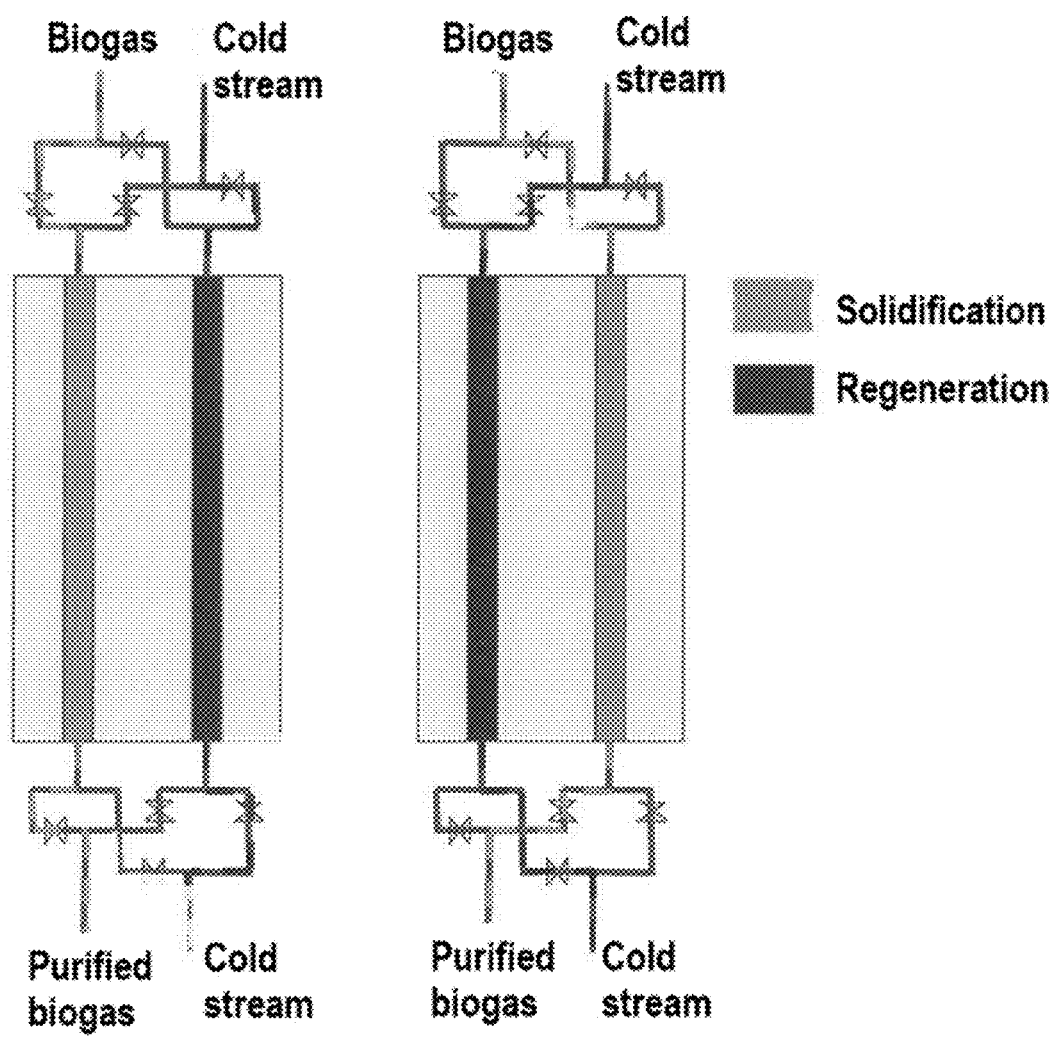
FIG. 2 is a schematic of an aspect of the invention.

As the case may be, the process according to the invention may have one or more of the following characteristics:

the second step of at least partial removal of said impurity comprises a first sub-step of compressing the dried biogas stream to a pressure of greater than 5 bar, preferably 10 bar; a second sub-step of solidifying said impurity by cooling the compressed biogas stream to a temperature below −70° C., and a third sub-step of depositing and removing said impurity. Preferably, this second step is cyclic so as to keep the process functioning continuously;

in the second sub-step, the biogas stream is cooled with a cooling stream, preferably a stream of $CO_2$, preferably produced during the third step.

in the third sub-step, said impurity is removed by sublimation of said impurity and flushing with a gaseous flushing stream.

the sublimation is performed at a temperature above the sublimation temperature and a pressure below 2 bar.

in the second sub-step, the biogas stream is cooled with a cooling stream, and in the third sub-step, the cooling stream obtained from the second sub-step is used as gaseous flushing stream.

preferably, the second sub-step and the third sub-step are performed simultaneously in the same sub-step;

the gaseous flushing stream is a stream of $CO_2$ or nitrogen.

the gaseous flushing stream is obtained from a storage capacity.

the gaseous flushing stream is the recycled $CO_2$ stream produced during the third step of separating the methane and the carbon dioxide contained in the biogas.

the third step of separating the methane and the carbon dioxide contained in the biogas is performed by washing with water or with amines, adsorption, solidification of the carbon dioxide or membrane separation.

the first step of drying of the biogas stream is performed by cooling and condensation followed by adsorption;

the second step of at least partial removal of said impurity uses a heat exchanger.

the first sub-step of compressing the biogas stream is performed using a compressor.

the second step of at least partial removal of said impurity uses a heat exchanger, in the second sub-step, the biogas stream is cooled with a cooling stream with the biogas stream passing through a first channel of the heat exchanger and the cooling stream passing through a second channel of the heat exchanger, and in the third sub-step, said impurity is removed by sublimation of said impurity and flushing with a gaseous flushing stream, with the gaseous flushing stream passing in the first channel of the heat exchanger; with the biogas stream passing in the second channel during the third sub-step. It is noted that the first channel is thus regenerated and that the second step can once again be performed cyclically. It is noted that, preferably, the flushing stream is a stream of $CO_2$ and the cooling stream is also a stream of $CO_2$. In this preferential case, the $CO_2$ stream passes in the second channel and then in the first channel via a set of valves. Similarly, the biogas stream passes in the first channel and then in the second channel via a set of valves. FIG. 2 illustrates this preferential case.

The first drying step is necessary to remove all traces of water from the biogas stream. The reason for this is that the water present in the biogas stream might be condensed in the compressor and damage it.

The second step of removing said impurity is preferably a cyclic process which functions in three sub-steps:

compression of the biogas stream to a pressure of greater than 5 bar, preferably 10 bar solidification in a heat exchanger of the impurities comprised in the biogas by cooling. Deposition of the impurities in the heat exchanger is thus observed. Purified biogas is recovered at the exchanger outlet.

sublimation of the impurities that have been deposited in the heat exchanger so as to regenerate the heat exchanger. The sublimation of the impurities takes place at low pressure, i.e. at a pressure of less than 2 bar. Preferably, a $CO_2$ stream is injected into the heat exchanger so as to flush out the impurities that have passed into the gaseous phase. The $CO_2$ simultaneously makes it possible to keep the biogas stream-$CO_2$ stream assembly cold.

The $CO_2$ may originate from a storage capacity or from the biogas itself. In the latter case, it would correspond to all or part of the $CO_2$ stream produced in the third step of the process according to the invention. It is noted that the $CO_2$ may be replaced with another gas such as nitrogen, etc.

Figure 3:
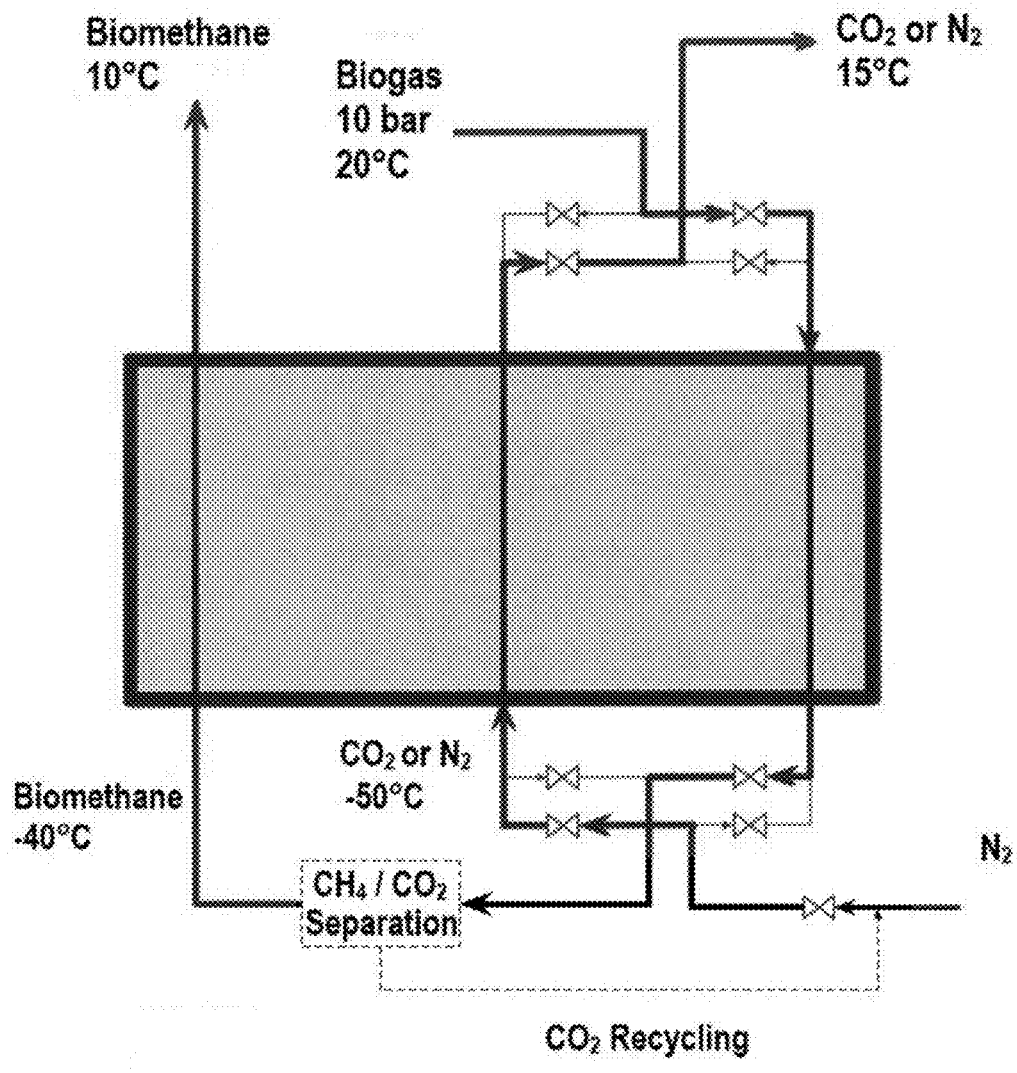
FIG. 3 is a schematic of another aspect of the invention.

At the heat exchanger outlet, the purified biogas may be depressurized, transformed into biomethane by separating the methane and the carbon dioxide, and then returned into the heat exchanger. FIG. 3 illustrates this return.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context dearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of" "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A process for producing biomethane from a biogas stream comprising methane, carbon dioxide and at least one impurity chosen from ammonia, volatile organic compounds, sulfur-based impurities ($H_2S$) and siloxanes, said process comprising the steps of:

drying the biogas stream to provide a dried biogas stream;

at least partially removing said at least one impurity contained in the dried biogas stream by solidification and removal of the solidified at least one impurity to yield at least partially purified biogas, wherein said step of at least partially removing said at least one of the at least one impurity comprises: i) compressing the dried biogas stream to a pressure of greater than 5 bar to provide a compressed dried biogas stream; ii) cooling the compressed dried biogas stream to a temperature below −70° C., thereby solidifying said at least one impurity resulting in deposition of the solidified at least one impurity; and iii) removing said solidified at least one impurity from the cooled dried compressed biogas stream to provide an at least partially purified biogas stream; and separating the methane and the carbon dioxide contained in the at least partially purified biogas so as to produce a biomethane stream and a $CO_2$ stream.

2. The process of claim 1, wherein the compressed biogas stream is cooled with a cooling stream of $CO_2$ produced during said step of separating.

3. The process of claim 1, wherein in said step of cooling, said at least one impurity is removed by sublimation of said at least one impurity and by flushing with a gaseous flushing stream.

4. The process of claim 3, wherein, the sublimation is performed at a temperature above a sublimation temperature and at a pressure below 2 bar.

5. The process of claim 3, wherein the cooling stream resulting from said step of cooling is used as the gaseous flushing stream.

6. The process of claim 5, wherein said steps of cooling and removal are performed simultaneously.

7. The process of claim 3, wherein the gaseous flushing stream is a stream of $CO_2$ or nitrogen.

8. The process of claim 7, wherein the gaseous flushing stream is obtained from a storage capacity.

9. The process of claim 7, wherein the gaseous flushing stream is a stream of recycled $CO_2$ produced during said step of separating.

10. The process of claim 1, wherein said step of separating is performed by washing with water, washing with amines, adsorption, solidification of the carbon dioxide, or membrane separation.

11. The process of claim 1, wherein said step of drying is performed by cooling and condensation followed by adsorption.

12. The process of claim 1, wherein said step of at least partially removing said impurity includes the use of a heat exchanger.

13. The process of claim 1, wherein said step of compressing is performed using a compressor.

14. The process of claim 12, wherein:
in said step of cooling, the biogas stream is cooled with a cooling stream with the biogas stream passing through a first channel of the heat exchanger and the cooling stream passing through a second channel of the heat exchanger; and
in said step of removing, said at least one impurity is removed by sublimation of said impurity and flushing with a gaseous flushing stream, with the gaseous flushing stream passing in the first channel of the heat exchanger and with the biogas stream passing in the second channel.

* * * * *